US00PP34271P2

(12) United States Plant Patent
van Langen

(10) Patent No.: US PP34,271 P2
(45) Date of Patent: May 24, 2022

(54) ***ECHEVERIA* PLANT NAMED 'AMIECH2008'**

(50) Latin Name: ***Echeveria setosa* Oliver x *Echeveria affinis* E. Walther.**
Varietal Denomination: AMIECH2008

(71) Applicant: Novoami B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 17/300,671

(22) Filed: Sep. 20, 2021

(30) Foreign Application Priority Data

Mar. 3, 2021 (QZ) ..... PBR 2021/0655

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373, 263.1
CPC ... A01H 5/12; A01H 5/02; A01H 5/00; A01H 6/32; A01H 6/00
See application file for complete search history.

(56) References Cited

PUBLICATIONS

Fern Farm Plants, retrieved on Oct. 26, 2021, retrieved from the Internet at https://fernfarmplants.com.au/products/echeveria-mensa?variant=12483681681519, 4 pp. (Year: 2021).*
Royal Botanic Gardens Kew Plants of the World Online, retrieved on Oct. 26, 2021, retrieved from the Internet at http://powo.science.kew.org/taxon/urn:lsid:ipni.org:names:86856-2, 3 pp. (Year: 2021).*

* cited by examiner

*Primary Examiner* — June Hwu
(74) *Attorney, Agent, or Firm* — Samuel R. McCoy, Jr.

(57) ABSTRACT

A new and distinct *Echeveria* hybrid plant named 'AMIECH2008' which is characterized by relatively small, obovate foliage that is tightly held in a compact rosette, green juvenile foliage at the center of the rosette which becomes progressively suffused with a mixture of greyed-purple to brown as it matures, foliage with a mucronate tip that becomes progressively suffused with greyed-purple with age, mature foliage that is lightly to moderately suffused with a mixture of greyed-purple to brown towards the apex of the abaxial surface, mature foliage that is heavily suffused with a mixture greyed-purple to brown on the adaxial surface, and the stability of these characteristics from generation to generation.

4 Drawing Sheets

Latin name of the genus and species: The Latin name of the genus and species of the novel variety disclosed herein is *Echeveria setosa* 'Oliver' x *Echeveria affinis* E. Walther.

Variety denomination: The inventive variety of *Echeveria* hybrid disclosed herein has been given the variety denomination 'AMIECH2008'.

CROSS REFERENCE TO RELATED APPLICATIONS

This application claims priority to the Community Plant Variety Rights application number 2021/0655, filed Mar. 3, 2021, which is herein incorporated by reference.

BACKGROUND OF THE INVENTION

Parentage: 'AMIECH2008' is an interspecific hybrid seedling selection resulting from the controlled pollination of an *Echeveria setosa* 'Oliver' plant (not patented), the seed parent, with an unnamed *Echeveria affinis* plant (not patented), the pollen parent. The crossing was made by the inventor in the spring of 2016 at a commercial greenhouse in Heerhugowaard, the Netherlands. In summer of 2017, one seedling was observed which exhibited unique growth and foliage characteristics. The seedling was isolated for further evaluation in order to confirm the distinctness and stability of the characteristics first observed. Upon confirmation of distinctness and stability, 'AMIECH2008' was selected for commercialization.

Asexual Reproduction: Asexual reproduction of the new cultivar 'AMIECH2008', by way of rooting leaf cuttings, was first initiated in the autumn of 2017 at the inventor's commercial greenhouse in Heerhugowaard, the Netherlands. Through six subsequent generations, the unique features of this cultivar have proven to be stable and true to type.

SUMMARY OF THE INVENTION

The cultivar 'AMIECH2008' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH2008'. These characteristics in combination distinguish 'AMIECH2008' as a new and distinct *Echeveria* hybrid cultivar:

1. 'AMIECH2008' exhibits foliage tightly arranged in a compact basal rosette which eventually forms a short, unbranched stem with age; and
2. 'AMIECH2008' exhibits small obovate foliage with a mucronate apex; and 3. 'AMIECH2008' exhibits green juvenile foliage at the center of the rosette which becomes progressively suffused with a mixture of greyed-purple and brown as it matures; and
4. 'AMIECH2008' exhibits mature foliage which is tipped with greyed-purple; and
5. 'AMIECH2008' exhibits mature foliage with a yellow-green adaxial surface that is lightly to moderately suffused with a mixture of greyed-purple and brown towards the apex; and
6. 'AMIECH2008' exhibits mature foliage with a greyed-purple to brown abaxial surface that is progressively suffused with brown towards the apex.

BOTANICAL DESCRIPTION OF THE PLANT

Figure 1:
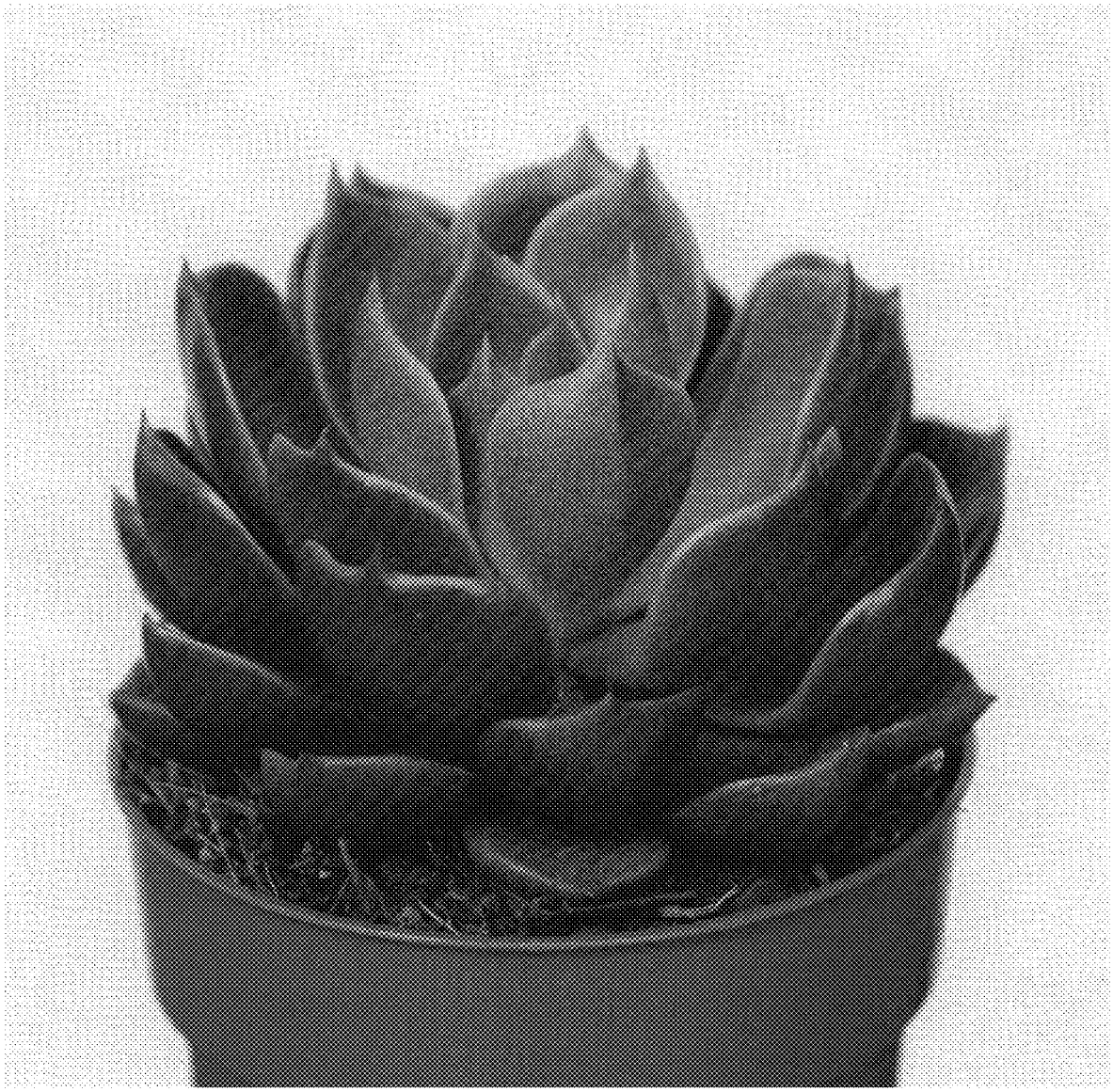
FIG. 1 illustrates, as nearly true as it is reasonably possible to make the same in color photographs of this type, an exemplary plant of 'AMIECH2008' grown in a commercial greenhouse. in Heerhugowaard, the Netherlands. This plant is approximately 26 week-old, shown planted in an 8.5 cm container.
Figure 2:
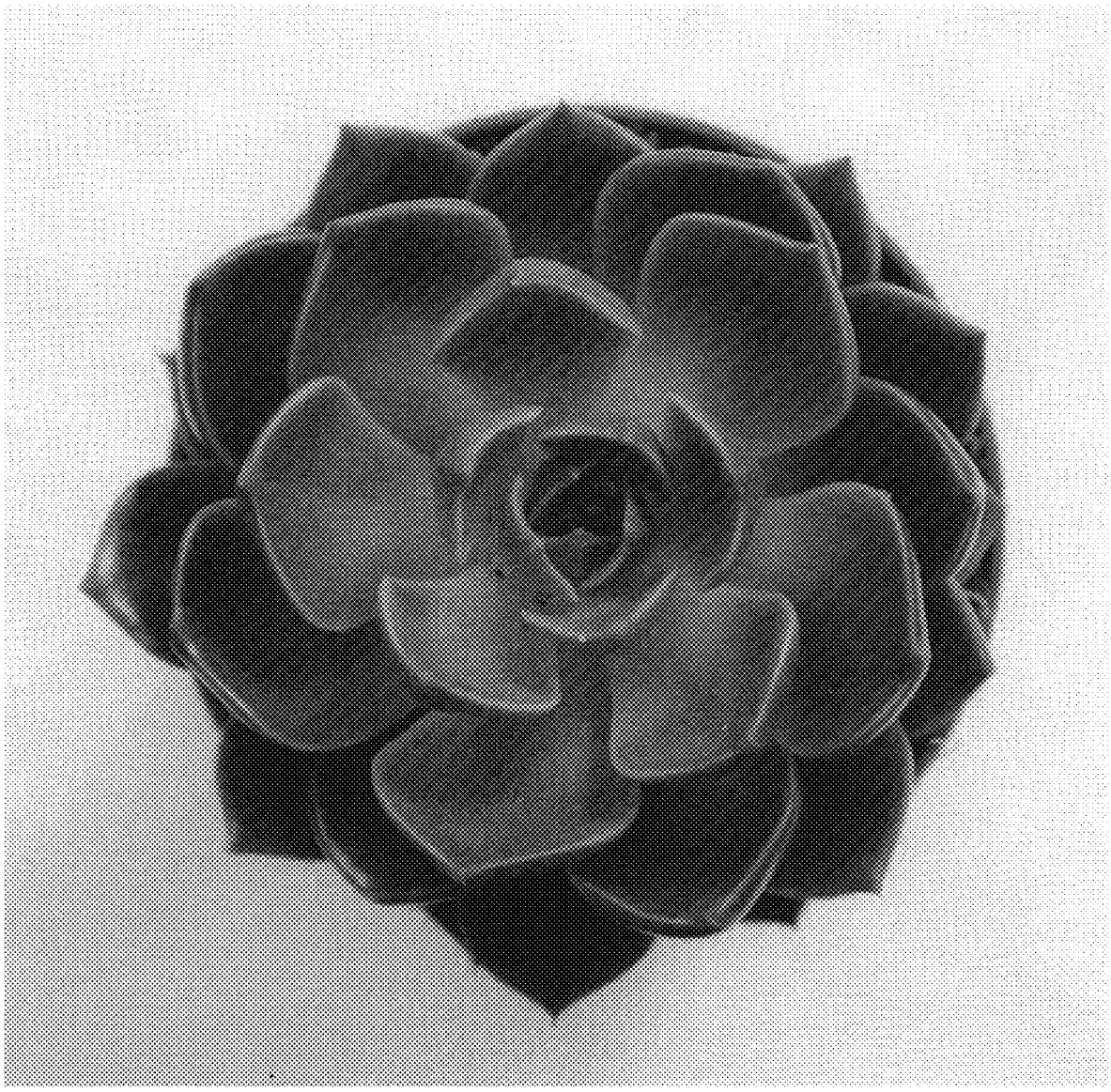
FIG. 2 illustrates, as nearly true as it is reasonably possible to make the same in color photographs of this type, the typical foliage arrangement of 'AMIECH2008'.
Figure 3:
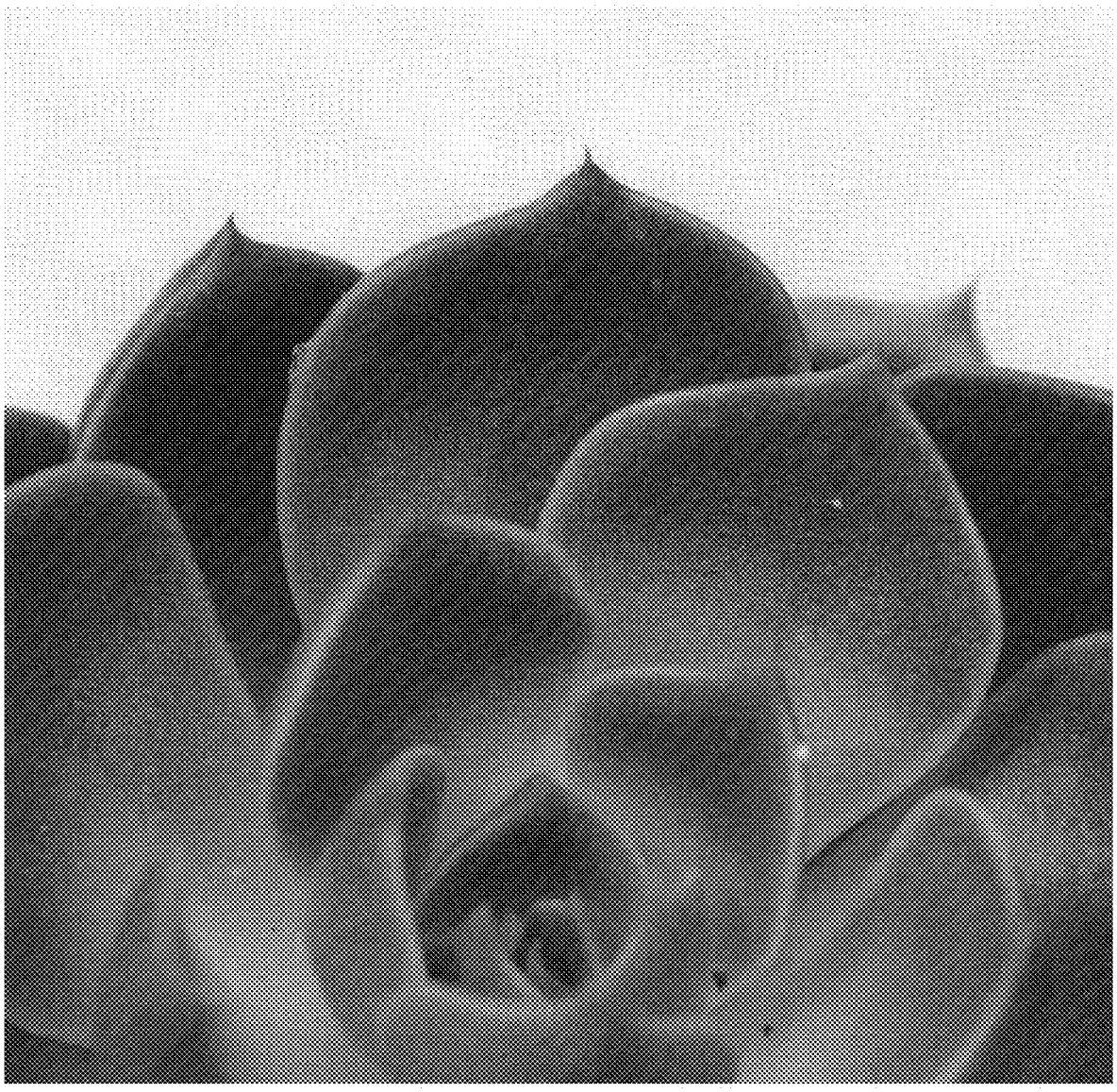
FIG. 3 illustrates, as nearly true as it is reasonably possible to make the same in color photographs of this type, the adaxial surface of the mature foliage 'AMIECH2008'.
Figure 4:
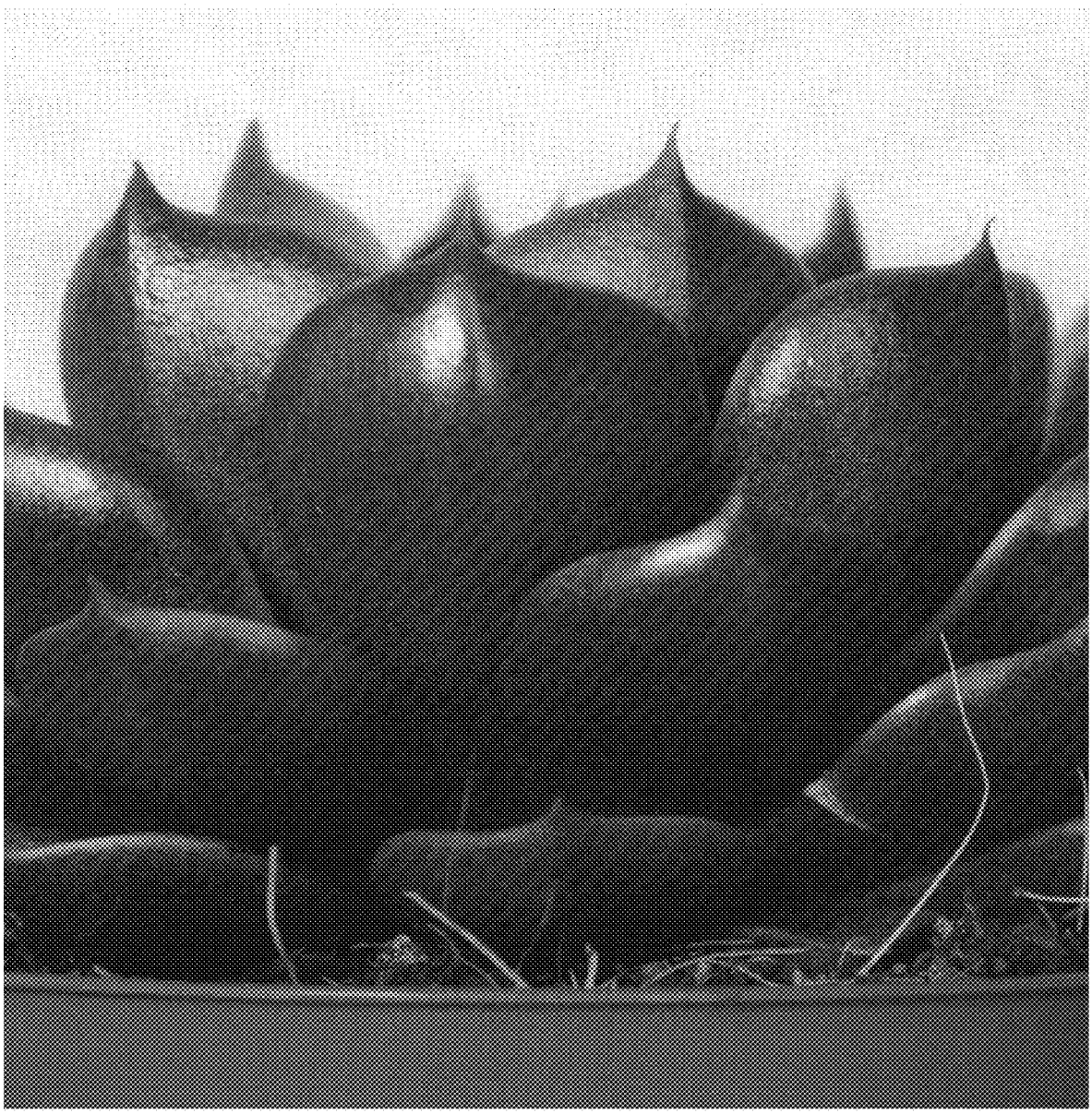
FIG. 4 illustrates, as nearly true as it is reasonably possible to make the same in color photographs of this type, the abaxial surface of the mature foliage 'AMIECH2008'.

The following observations and measurements made in June of 2021 describe averages from a sample set of six specimens of 26 week-old 'AMIECH2008' plants grown in 8.5 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and Botrytis as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH2008' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH2008' and comparisons with the parent plants and closest known comparator are provided below.

Plant description:

*Growth habit*.—Succulent perennial with foliage growing in a non-branched basal rosette.

*Plant shape*.—Flattened globular.

*Height from soil level to top of foliar plane*.—6.1 cm.

*Plant spread*.—Average of 9.3 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 25 weeks to produce a marketable plant in an 8.5 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a basal rosette, eventually forming a short, unbranched stem with age; no lateral branching.

*Quantity of main stems*.—1.

*Quantity of lateral branches*.—None.

*Main stem dimensions*.—2.9 cm long and 1.0 cm in diameter.

*Internode length*.—0.1 cm.

*Cross section*.—Rounded.

*Aspect*.—Nearly vertical.

*Strength*.—Moderately strong.

*Texture and luster*.—Smooth, glaucous, and slightly glossy.

*Color, when developing*.—Yellow-green, nearest to RHS 147D yet lighter.

*Color of mature stem*.—Yellow-green, nearest to RHS 147D.

*Color at internodes*.—Yellow-green, nearest to RHS 147D.

Foliage:

*Arrangement*.—Rosette.

*Division*.—Simple.

*Attachment*.—Sessile.

*Quantity*.—Approximately 47 leaves per rosette.

*Shape*.—Obovate.

*Dimensions*.—4.6 cm long, 1.6 cm wide, and 0.6 cm thick, on average.

*Aspect*.—Moderately concave with leaf tips slightly curled upward.

*Attitude*.—Juvenile foliage at the center of the rosette is held upward and outward; foliage becomes progressively more relaxed towards the outer whorls of mature foliage.

*Apex*.—Mucronate.

*Base*.—Cuneate.

*Margin*.—Entire; margins are not undulate.

*Pubescence, texture and luster of the adaxial surface*.—Smooth, glabrous, and glossy.

*Pubescence, texture and luster of the abaxial surface*.—Smooth, glabrous, and glossy.

*Luster of the adaxial surface*.—Moderately glossy.

*Luster of the abaxial surface*.—Moderately glossy.

*Color*.—Juvenile foliage, adaxial surface — Green, nearest to a RHS 138A, and fading to yellow-green towards the base, nearest to RHS 145D; tipped and narrowly margined with a translucent yellow-green, nearest to RHS 145A. Juvenile foliage, abaxial surface — Green, nearest to a mixture of RHS 138A and 138B, and fading to yellow-green towards the base, nearest to RHS 145C; tipped and narrowly margined with a translucent yellow-green, nearest to RHS 145A. Mature foliage, adaxial surface — Yellow-green, nearest to RHS 147A, and fading to a lighter shade of yellow-green towards the base, nearest to RHS 146D; suffused with a mixture of greyed-purple and brown towards the apex, nearest to RHS 183A and 200B; narrowly margined yellow-green, distally, nearest to RHS 145A; tipped greyed-purple, nearest to RHS 183C. Mature foliage, abaxial surface — Nearest to a mixture of greyed-purple and brown, RHS 183A and 200B, and fading to yellow-green towards the base, nearest to RHS 146D; narrowly margined yellow-green, distally, nearest to RHS 145A, and becoming progressively suffused with brown towards the apex, nearest to RHS 200D; tipped greyed-purple, nearest to RHS 183C. Venation, adaxial surface — No visible venation. Venation, abaxial surface — No visible venation.

*Petiole*.—No petiole; leaves are sessile.

Inflorescence: No flowering has been observed to date.

COMPARISONS WITH THE PARENT PLANTS AND CLOSEST KNOWN COMPARATOR

Plants of the new cultivar 'AMIECH2008' differ from the seed parent, an *Echeveria setosa* 'Oliver' plant (not patented), in the following characteristics described in Table 1 below.

TABLE 1

| Characteristic | 'AMIECH2008' | The seed parent. |
|---|---|---|
| Foliage dimensions. | Shorter and broader, relative to the seed parent. | Longer and narrower, relative to 'AMIECH2008'. |
| Foliage pubescence. | Glabrous. | Pubescent. |
| General coloration of the abaxial surface of the mature foliage. | A mixture of greyed-purple and brown, and becoming progressively suffused with brown towards the apex; tipped greyed-purple. | Light green and tipped red. |

Plants of the new cultivar 'AMIECH2008' differ from the pollen parent, an unnamed *Echeveria affinis* plant (not patented), in the following characteristics described in Table 2 below.

TABLE 2

| Characteristic | 'AMIECH2008' | The pollen parent. |
|---|---|---|
| Foliage length. | Shorter than the pollen parent. | Longer than 'AMIECH2008'. |
| General coloration of the foliage. | The adaxial surface is generally green, with older leaves moderately suffused with a mixture of greyed-purple and brown towards the apex; the abaxial surface is mixture of greyed-purple and brown, and becoming progressively suffused with brown towards the apex; tipped greyed-purple. | The adaxial surface is green with most of the lamina very heavily suffused with greyed-purple to black; the abaxial surface is greyed-purple to black. |

COMPARISONS WITH THE CLOSEST KNOWN COMPARATOR

Plants of the new cultivar 'AMIECH2008' differ from the closest known commercial comparator, *Echeveria* 'Mensa' (not patented), in the following characteristics described in Table 3 below.

TABLE 3

| Characteristic | 'AMIECH2008' | 'Mensa' |
|---|---|---|
| Growth habit. | More compact, relative to 'Mensa'. | Less compact, relative to 'AMIECH2008'. |
| General coloration of leaf tips. | Greyed-purple, | A mixture of greyed-green and greyed-purple. |

That which is claimed is:

1. A new and distinct variety of *Echeveria* hybrid plant named 'AMIECH2008', substantially described and illustrated herein.

* * * * *